United States Patent [19]

Davis et al.

[11] Patent Number: 5,041,670
[45] Date of Patent: Aug. 20, 1991

[54] PREPARATION OF N-ARYL AMINES FROM ISOCYANATES

[75] Inventors: Franklin A. Davis, Wynnewood; William E. Starner, Freeland, both of Pa.

[73] Assignee: Drexel University, Philadelphia, Pa.

[21] Appl. No.: 174,663

[22] Filed: Mar. 29, 1988

[51] Int. Cl.[5] ............................................ C07E 209/00
[52] U.S. Cl. ..................................................... 564/414
[58] Field of Search ................................. 564/305, 414

[56] References Cited

U.S. PATENT DOCUMENTS 4,078,002 3/1978 Brown ................................. 564/487
4,160,784 7/1979 Sugasawa et al. .................. 564/305

OTHER PUBLICATIONS

Brown et al., "Selective Reductions. XXI. 9-Borabicyclo[3.3.1] nonane in Tetrahydrofuran as a New Selective Reducing Agent in Organic Synthesis, Reaction with Selected Organic Compounds Containing Representative Functional Groups", *Journal of Organic Chemistry*, vol. 41, No. 10, pp. 1778–1791 (1976).

R. G. Arnold et al., *Recent Advances in Isocyanate Chemistry*, pp. 47, 51 and 116 (1956).

*Primary Examiner*—C. Warren Ivy
*Assistant Examiner*—Raymond Covington
*Attorney, Agent, or Firm*—Panitch Schwarze Jacobs & Nadel

[57] ABSTRACT

Methods of producing N-phenyl amines comprise reacting a phenyl-containing isocyanate with HR, and a boron complexing agent in an aprotic solvent, wherein R, is —OH or —COOH (i.e., water or formic acid), neutralizing the resulting N-aryl amide to N-aryl amine and recovering the N-aryl amine.

18 Claims, No Drawings

PREPARATION OF N-ARYL AMINES FROM ISOCYANATES

FIELD OF THE INVENTION

The present invention relates to a method of producing N-phenyl amines from phenyl-containing isocyanate compounds.

RELATED APPLICATIONS

The present application is related to our copending U.S. patent applications for "Preparation of N-Aryl Formamides from Isocyanates and Formamides Produced Thereby," Ser. No. 174,661, and "Preparation of N-Aryl Amides from Isocyanates," Ser. No. 174,662, both filed concurrently herewith.

BACKGROUND OF THE INVENTION

The preparation of amines from isocyanates dates back to the late 1800's and several methods have been exercised. For example, Hofmann, *Ann. Chem. Pharm.*, 74:13 (1850) described the reaction of isocyanates with hydrochloric or sulphuric acid resulting in substantially quantitative yields of the amine salt and Gumpert, *J. F. Prakt. Chemie*, 31:121 (1885) described the hydrolysis of isocyanates to amines using an alkali hydroxide solution. Naegeli and Tyabji, *Helv. Chim. Acta.* 16:349 (1933) examined Gumpert's reaction and discovered that a carbamic acid salt is formed as an intermediate. Further, U.S. Pat. Nos. 4,386,218; 4,418,160; 4,501,873; 4,569,982; 4,540,720; 4,565,645; and 4,515,982, issued to Rasshofer et al., disclose the production of polyamines by the alkaline hydrolysis of compounds containing terminal isocyanate groups, including isocyanate prepolymers.

Chlorotoluenediamine has been produced from chlorotoluene diisocyanate as disclosed by U.S. Pat. No. 3,752,790, issued to McShane et al. McShane, however, first chlorinates the diisocyanate and then hydrolyzes the isocyanate groups with strong mineral acids, which are difficult to handle.

The production of N-formyl compounds from formamide and a primary or secondary alkyl or aryl amine using boric acid as a catalyst has been described in U.S. Pat. No. 3,347,916, issued to Huber. In addition, the reaction of aryl isocyanates with formic acid in the absence of a boron compound has been studied to some extent. U.S. Pat. No. 4,417,001, issued to Liessem, for example, describes the use of carbon dioxide generated from a carboxylic acid/isocyanate reaction as a polyurethane foam blowing agent. Similarly, U.S. Pat. No. 3,350,438, issued to Hennig, describes a process for the preparation of a biuret polyisocyanate by reacting organic polyisocyanate with anhydrous formic acid.

Further, U.S. Pat. No. 3,799,963, issued to Adams, describes a process for reducing the hydrolyzable chloride and acidic content of an organic isocyanate. The process comprises heating the organic isocyanate to a temperature above about 100° C. but below the decomposition temperature of the organic isocyanate in the presence of formic acid or a formic acid derivative selected from the group consisting of N,N'-diformyltoluenediamine, an adduct of toluenediisocyanate and formic acid. The toluene diisocyanate (TDI)-formic acid adduct, described in Adams' Example 6, for example, was prepared by reacting 80/20 2,4-/2,6-TDI with anhydrous formic acid in anhydrous ether. A white precipitate was filtered and washed with ether, yielding a white crystal having a melting point of 96°-97° C., which by elemental analysis had the empirical formula $C_{10}H_8N_2O_4$ rather than the monoformamide $C_9H_8N_2O_2$ or the diformamide, $C_9H_{10}N_2O_2$. Our efforts to repeat this isolation have indicated that an adduct is not formed, but a formamide results.

U.S. Pat. No. 4,105,686, issued to Raes et al., describes the use of carboxylic acids to deactivate a toluenediisocyanate distillation residue to an inert granular solid at elevated temperatures from 120° C. to about 200° C. No product composition or structure is discussed.

Potts and Stalioraitis, in their U.S. Pat. No. 3,592,854, describe a process to hydrolyze amides to amines using water and caustic in large amounts of a lower aliphatic primary alcohol. U.S. Pat. No. 3,922,304, issued to Schreyer, similarly describes the conversion of formanilides to amines by hydrolysis or alcoholysis.

None of the prior art methods involve the preparation of phenyl amines from isocyanate, formic acid or water and a boron complexing agent. Moreover, the methods of the prior art require expensive and difficult to use reagents, which generally produce poor yields and high by-product formation.

In view of the serious deficiencies and inefficiencies of the prior art, it would be desirable to have a method to produce N-phenyl amines efficiently, cheaply and with little or no byproduct formation.

BRIEF SUMMARY OF THE INVENTION

According to the present invention, methods of producing N-phenyl amines comprise reacting a phenyl-containing isocyanate compound with HR', wherein R' is —OH or —COOH (i.e., water or formic acid), and a boron complexing agent in an aprotic solvent, where HR' and the boron complexing agent are each present in an at least about molar equivalent to the phenyl-containing isocyanate compound, neutralizing the resulting N-phenyl amide complex to N-phenyl amine and recovering the desired N-aryl amine. Preferably, neutralizing occurs in the presence of an aqueous base.

DETAILED DESCRIPTION OF PREFERRED EMBODIMENTS

In accordance with the present invention, a phenyl-containing isocyanate compound is reacted with HR', wherein R' is —OH or —COOH, and a boron complexing agent. Preferably, the phenyl-containing isocyanate compound is of the formula:

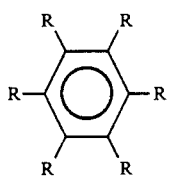

wherein at least one R group is NCO and the remaining R groups are selected from the group consisting of hydrogen, alkyl, aryl, alkylaryl, arylalkyl (aralkyl), halogen, carboxylic acid, ester linkage, amide and nitrile.

Examples of suitable phenyl-containing isocyanates to produce amines according to the present invention include: phenyl isocyanate, tolyl isocyanate, nitrophenyl isocyanate, m-phenylene diisocyanate, p-phenylene diisocyanate, 2,4-toluene diisocyanate, 2,6-toluene diisocyanate, chlorotoluene diisocyanate, methylene bis(phenyl isocyanate), also known as MDI, and polyisocyanate prepolymers described by Rasshofer in U.S. Pat. Nos. 4,386,218; 4,418,160; 4,501,873; 4,515,923; 4,540,720; 4,545,645; and 4,569,982. It will be appreciated by one skilled in the art, however, that other, similar phenyl-containing isocyanates may be used as the phenyl-containing isocyanate compound reagent in accordance with the invention.

The phenyl-containing isocyanate compound is reacted with a compound of the formula HR', where R' is —OH or —COOH, namely, water or formic acid. Commercially available formic acid of varying grades, such as 98% formic acid or anhydrous (i.e., less than 2% by weight water content) formic acid may be used. In addition, mixtures of water and formic acid may also be used in accordance with present invention. Where R' is —OH, it is preferred that the $H_2O$ is distilled. One skilled in the art will recognize, however, that non-distilled water may be used in accordance with the present invention.

Further, according to the present invention, the phenyl-containing isocyanate compound and HR' are reacted with a boron complexing agent. Preferably, the boron complexing agent is a boron halide, such as boron trifluoride, boron trichloride, boron tribromide or boron iodide, an organic boron complex, such as $BF_3 \cdot (C_2H_5)_2O$, $BF_3 \cdot (CH_3)_2O$, $BF_3 \cdot (CH_3)_2S$, $BCl_3 \cdot (CH_3)_2S$, or $BBr_3 (CH3)2S$, boron oxide or boric anhydride. A particularly preferred complexing agent is boron trifluoride etherate. One skilled in the art will recognize, however, that other compounds may be used as the boron complexing agent in accordance with the present invention.

The reaction occurs in an aprotic solvent. The aprotic solvent is present in an amount sufficient to allow mobility and/or solubility of the reagents. One skilled in the art may readily determine the quantity of aprotic solvent to be used according to the methods of the present invention. Examples of suitable aprotic solvents include methylene chloride, chloroform, benzene, toluene, xylene, ethyl ether, methyl ether, tetrahydrofuran, p-dioxane and acetonitrile. One skilled in the art will appreciate, however, that other aprotic solvents may be used in accordance with the present invention.

The reaction may occur at temperatures up to about 100° C. or the boiling point of the solvent, if the boiling point of the solvent is lower than 100° C. It has been found that higher reaction temperatures decrease the reaction time necessary to synthesize the desired product. Conversely, lower temperatures increase the reaction time or, at low extremes, inhibit the reaction of the present invention. Generally, reaction temperatures below about 0° C. and above about 100° C. are undesirable. One skilled in the art will appreciate that in this preferred range of reaction temperatures, energy input, in the form of heat, is reduced or eliminated relative to the prior art. In addition, heat sensitive materials, reagents and products may be used or obtained using the methods of the invention.

It may be desired to conduct the reaction according to the present invention in a vessel under reflux to recover volatilized reactants and solvents during the reaction. One skilled in the art may readily determine the techniques and apparatus useful for reflux reactions. Preferably, the reaction mixture is continuously agitated with a magnetic stirrer or other agitation means known in the art. In addition, because gas is evolved during the reactions of the present invention, it may be desirable to equip the reaction vessel with a vent tube or inert gas purge, such as a nitrogen purge, to rid or collect the evolved gas. One skilled in the art may readily determine the techniques and equipment desirable for this purpose in accordance with the invention.

HR' and the boron complexing agent are each present in an at least about molar equivalent to the isocyanate moieties or functions of the phenyl-containing isocyanate compound. Preferably, the molar ratio of isocyanate moieties of the phenyl-containing isocyanate compound to HR' is about 1:1 to about 1:100 More preferably, the molar ratio of isocyanate moieties of the phenyl-containing isocyanate compound to HR is about 1:1. Similarly, the molar ratio of isocyanate moieties of the phenyl-containing isocyanate compound to boron complexing agent is preferably about 1:1 to about 1:100. More preferably, the molar ratio of isocyanate moieties of the phenyl-containing isocyanate compound to boron complexing agent is about 1:1. It will be appreciated by one skilled in the art that as the number of isocyanate moieties on the phenyl-containing isocyanate reagent increases, the amount of formic acid and boron complexing agent should each generally be increased.

As discussed below, the product formed using the reactants of the present invention is in the form of a boron agent/amide complex. The complex generally precipitates out of the reaction mixture and may be isolated by evaporation or filtration. One skilled in the art may readily determine the conventional methods to isolate the boron agent/amide complex. Once isolated, the complex is, according to one embodiment of the present invention, dissolved in a solvent, such as water, where neutralization of the complex will occur. In another embodiment of the present invention, the complex is dissolved in a neutralizing solution, such as an aqueous sodium carbonate solution. It will be understood by one skilled in the art that other solvents may be used to dissolve the boron agent/amide complex.

Neutralization of the boron/amide complex readily yields the phenyl amine (in the case of an N-phenyl monoamine, also called aniline). Preferably, the neutralization occurs in the presence of an aqueous base. Examples of suitable aqueous bases include sodium carbonate, sodium bicarbonate and sodium hydroxide. It will be recognized by one skilled in the art, however, that other aqueous bases may be used in accordance with the present invention.

The course of the reaction may be followed by infrared spectroscopy or by the volume of carbon dioxide gas evolved. Preferably, the reaction is allowed to proceed until the evolution of carbon dioxide gas and/or carbon monoxide substantially ceases. Analysis of the resulting product may be conducted using conventional techniques, such as gas-liquid chromatography, high-performance liquid chromatography and combustion elemental analysis. The purity of the product formed may generally be determined by the melting point of the product as compared to theoretical or known melting point values. One skilled in the art will recognize that other analytical methods may be used to quantify and qualify the resulting product.

Because of the efficiency of the methods of the present invention, isolation of the desired amine product may be easily accomplished by methods known in the art, including vacuum extraction, distillation, or recrystallization. In one embodiment of the present invention, it is desirable to use separation extraction to isolate the desired amine. For example, where an aqueous base is used to neutralize the amide to the desired amine, methylene chloride, for example, may be added to perform separation or solvent extraction to remove any impurities. One skilled in the art will recognize, however, that other isolation techniques may be used in accordance with the present invention.

N-phenyl amines resulting from the claimed methods of the present invention are generally produced in excess of an about 80% yield. This surprisingly high yield indicates a lack of side reactions and by-products, often present in the prior art. In addition, product purity is generally in excess of 90%. The high yield and high purity achieved using these methods help to reduce the quantity and cost of raw materials required to produce the desired N-phenyl amine.

While the inventors do not wish to be limited by any particular theory, it is believed that boron compounds tend to complex with various oxygen containing compounds. For example, a boron compound, such as $BF_3$, reacts with formic acid and water in the following manner:

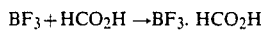

$$BF_3 + HCO_2H \rightarrow BF_3 \cdot HCO_2H$$

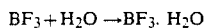

$$BF_3 + H_2O \rightarrow BF_3 \cdot H_2O$$

Isocyanates react with formic acid and carbamic acid, respectively. Where a boron complexing agent, such as $BF_3$ is present, a new complex is formed:

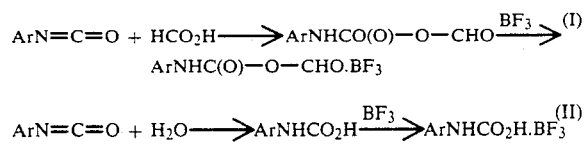

The mixed anhydride intermediate shown in Equation I and the carbamic acid shown in Equation II may undergo intramolecular rearrangement and elimination, releasing carbon dioxide gas, as illustrated in Equations III and IV. Where a boron complexing agent is present in the mixed anhydride, carbon monoxide gas is also released, as illustrated in Equation III:

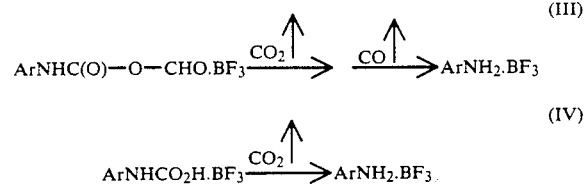

Neutralization of the boron/amide complex using, for example, an aqueous base yields the desired aryl amine.

The invention will now be illustrated in further detail by reference to the following, specific, non-limiting examples All parts are parts by weight unless otherwise indicated.

EXAMPLE 1

20 parts Of freshly distilled ethyl ether were placed in a vessel equipped with a $N_2$ purge, a dropping funnel, a magnetic stirrer, a thermometer and a condenser. 1.19 parts (0.01 mole) of phenyl isocyanate and 1.41 parts (0.01 mole) of boron trifluoride etherate were added with stirring. 0.18 part (0.01 mole) of distilled water were added to the reaction mixture. The reaction mixture was heated to about 30° C. under reflux until gas ($CO_2$) evolution had ceased after approximately four hours. The volatiles were removed on a rotary evaporator, leaving a white solid. 20 ml of distilled water were added to dissolve the solid. The solid was neutralized with a saturated sodium carbonate solution. The product was extracted from the neutralization solution with 20 ml methylene chloride. 0.85 part of aniline (91% yield) was recovered.

EXAMPLE 2

20 parts toluene, 5.0 parts (0.04 mole) boron trifluoride etherate and 1.19 parts (0.01 mole) phenyl isocyanate were added in a vessel as described in Example 1. After stirring, 1.0 part (0.02 mole) 98% formic acid was added and allowed to react, as in Example 1, for about two hours until gas generation had ceased. The solvent was removed by distillation, leaving a white powder. The white powder was added to 20 parts of saturated sodium carbonate solution and the solution was then extracted with 20 parts of methylene chloride. Removal of the methylene chloride solution yielded 0.87 part of aniline (93% yield).

EXAMPLE 3

20 parts freshly distilled ether, 1.74 parts (0.01 mole) 2,6-toluenediisocyanate, 2.8 parts (0.02 mole) boron trifluoride etherate and 1.0 part (0.02 mole) 98% formic acid were added and reacted following the procedures of Example 1. The neutralizing and isolation procedures described in Example 2 were followed. 1.16 g (94% yield) 2,6-toluenediamine were recovered, having a melting point of 104° C. to 105° C.

EXAMPLE 4

20 parts freshly distilled ether, 1.74 parts (0.01 mole) 2,4-toluene-diisocyanate, 2.8 parts (0.02 mole) boron trifluoride etherate and 1.0 part (0.02 mole) 98% formic acid were combined and reacted as described in Example 1. Neutralization and isolation procedures described in Example 2 followed. 1.19 g (98% yield) 2,4-toluenediamine were recovered, having a melting point of 97° C.–98° C.

EXAMPLE 5

20 parts freshly distilled ether, 1.74 parts (0.01 mole) 2,4-toluenediisocyante, 2.8 parts (0.02 mole) boron trifluoride etherate and 0.40 part (0.02 mole) distilled water were combined and reacted as in Example 1. Neutralization and isolation procedures described in Example 2 were conducted. 1.09 g (89% yield) 2,6-toluenediamine were recovered having a melting point of 103° C.–105° C.

EXAMPLE 6

20 parts toluene, 1.74 parts (0.01 mole) 2,4-toluenediisocyanate, 2.8 parts (0.02 mole) boron trifluoride etherate and 0.40 part (0.02 mole) distilled water were combined and reacted as described in Example 1. The neutralization and isolation procedures described in Example 2 were conducted. 1.17 parts (97% yield) 2,4-toluenediamine were recovered having a melting point of 96° C.–98° C.

EXAMPLE 7

0.5 part (0.01 mole) $B_2O_3$, 25 ml methylene chloride, 1.19 parts (0.01 mole) phenyl isocyanate and 0.47 part (0.01 mole) anhydrous formic acid were combined and reacted as described in Example 1. The reaction mixture was stirred for 18 hours and the precipitated solids were collected by filtration. The solids were dissolved in 25 ml of distilled water. The solution was neutralized with a saturated sodium carbonate solution and the solution was washed with two 25 ml portions of ethyl ether. After drying the ether solution over anhydrous sodium sulfate, the solvent was removed, leaving 0.90 parts aniline (98% yield).

EXAMPLE 8

(Comparative)

20 ml toluene, 1.19 parts (0.01 mole) phenyl isocyanate, 1.0 part (0.02 mole) 98% formic acid and 0.47 part (0.003 mole) boron trifluoride etherate were combined and reacted as described in Example 1. The neutralization and isolation techniques described in Example 2 were conducted. 1.09 parts of a mixed product were recovered. Proton nuclear magnetic resonance analysis identified 84.5% formanilide and 15.5% aniline. It is believed that the catalytic amount of boron trifluoride yields the amide instead of the amine achieved when the boron complexing agent is present in the preferred ratios.

EXAMPLE 9

(Comparative)

20 parts toluene, 1.19 parts (0.01 mole) phenyl isocyanate and 0.50 part (0.01 mole) 98% formic acid were combined and reacted as described in Example 1. The isolation techniques described in Example 2 were conducted. 1 16 g (99% yield) formanilide were recovered having a melting point of 45° C.–46° C. The amide is produced with these reactants in the absence of a boron complexing agent.

EXAMPLE 10

(Comparative)

20 parts freshly distilled ether, 1.19 parts (0.01 mole) phenyl isocyanate and 0.19 part (0.01 mole) of water were combined and reacted as described in Example 1. The isolation techniques described in Example 2 were conducted. 0.70 part (94% yield) diphenylurea was recovered having a melting point of 253° C. An isocyanate and water produce urea in the absence of a boron complexing agent.

EXAMPLE 11

(Comparative)

1.19 (0.01 mole) parts phenyl isocyanate, 1.44 parts (0.01 mole) boron trifluoride etherate and 0.70 part (0.011 mole) acetic acid were combined and reacted as described in Example 1. After 18 hours, 20 parts methylene chloride were added and the reaction mixture was stirred for an additional two hours. The solvent was removed by distillation, leaving a solid. 20 parts of a saturated sodium carbonate solution were added and the precipitated solids were collected by filtration and washed with distilled water. After drying, 1.25 parts (95% yield) acetanilide were recovered having a melting point of 114° C. to 116° C. Higher carboxylic acids used in place of formic acid or water are believed to result in the amide, as occurred here.

EXAMPLE 12 (Comparative)

25 parts toluene were placed in a vessel described in Example 1. 0.64 part (0.02 mole) anhydrous hydrogen chloride were sparged into the toluene solution. 1.19 parts (0.01 mole) phenyl isocyanate and 1.0 part (0.02 mole) 98% formic acid were added to the solution. The reaction mixture was heated to 116° C. under reflux and stirred for 18 hours. The solution was filtered, yielding 0.80 parts aniline hydrochloride. The toluene solvent was removed on a rotary evaporator and 20 parts saturated sodium carbonate solution and 20 parts methylene chloride were added to the residue. After removing the solvent, 0.30 part (27% yield) formanilide was recovered having a melting point of 46°–47° C. The anhydrous hydrogen chloride substitution for the boron complexing agent is believed to be the cause of amide formation.

EXAMPLE 13

(Comparative)

30 parts methylene chloride, 1.19 parts (0.01 mole) phenyl isocyanate, 1.05 parts (0.01 mole) phosphorous oxychloride and 0.50 part (0.01 mole) 98% formic acid were combined and reacted as described in Example 1. After stirring for 18 hours, 20 parts saturated sodium carbonate solution were added and the organic layer was separated, rotary evaporated and dried. 0.95 part (92% yield) formanilide was recovered having a melting point of 45°–46° C. Phosphorous oxychloride, in place of the boron complexing agent, caused the formation of the amide.

EXAMPLE 14

(Comparative)

20 parts methylene chloride, 1.33 parts (0.01 mole) aluminum chloride and 1.19 parts (0.01 mole) phenyl isocyanate were placed into the vessel described in Example 1. No reaction was observed. 0.62 part (0.014 mole) 98% formic acid was added, which resulted in a vigorous reaction. The reaction mixture was stirred for 18 hours. 20 parts saturated sodium carbonate solution was added and the organic layer was separated and dried. The solvent was removed on a rotary evaporator, leaving 0.91 parts phenyl isocyanate indicating the lack of reaction with phenyl isocyanate using these reagents and conditions.

EXAMPLE 15

(Comparative)

20 parts methylene chloride, 1.19 parts (0 01 mole) phenyl isocyanate, 1.66 parts (0.01 mole) ferric chloride and 0.62 part (0.014 mole) 98% formic acid were combined and reacted as described in Example 1. The solvent was removed on a rotary evaporator leaving 0.75 g of phenyl isocyanate, indicating the lack of a reaction with phenyl isocyanate using these reagents and conditions.

The present invention may be embodied in other specific forms without departing from the spirit or essential attributes thereof and, accordingly, reference should be made to the appended claims, rather than the specification, as indicating the scope of the invention.

We claim:

1. The method of producing N-phenyl amines of the formula $ArNH_2$, which comprises reacting a phenyl-containing isocyanate with HR' and a boron complexing agent, in aprotic solvent, wherein R' is —OH or —COOH, and where HR' and the boron complexing agent are each present in an at least about molar equivalent to the phenyl-containing isocyanate compound, neutralizing the resulting N-phenyl amide to N-phenyl amine, and recovering the N-phenyl amine.

2. The method according to claim 1, wherein the phenyl-containing isocyanate compound is of the formula:

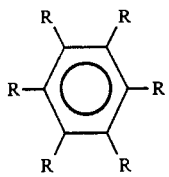

wherein at least one R group is NCO and the remaining R groups are selected from the group consisting of hydrogen, alkyl, aryl, alkylaryl, arylalkyl, halogen, carboxylic acid, ester linkage, amide and nitrile.

3. The method according to claim 2, wherein the phenyl-containing isocyanate compound is selected from the group consisting of phenyl isocyanate, tolyl isocyanate, nitrophenyl isocyanate, m-phenylene diisocyanate, p-phenylene diisocyanate, 2,4-toluene diisocyanate, 2,6-toluene diisocyanate, chlorotoluene diisocyanate, methylene bis(phenyl isocyanate) and polyisocyanate prepolymers.

4. The method according to claim 1, wherein the boron complexing agent is a boron halide.

5. The method according to claim 4, wherein the boron halide is selected from the group consisting of boron trifluoride, boron trichloride, boron tribromide and boron iodide.

6. The method according to claim 1, wherein the boron complexing agent is an organic boron complex.

7. The method according to claim 6, wherein the organic boron complex is selected from the group consisting of $BF_3 \cdot (C_2H_5)O_2$, $BF_3 \cdot (CH_3)_2O$, $BF_3 \cdot (CH_3)_2S$, $BCl_3 \cdot (CH_3)_2S$, and $BBr_3 \cdot (CH_3)_2S$.

8. The method according to claim 1, wherein the boron complexing agent is selected from the group consisting of boron oxide and boric anhydride.

9. The method according to claim 1, wherein the stoichiometric ratio of isocyanate moieties of the phenyl-containing isocyanate compound to HR' is about 1:1 to about 1:100.

10. The method according to claim 1, wherein the stoichiometric ratio of isocyanate moieties of the phenyl-containing isocyanate compound to HR' is about 1:1.

11. The method according to claim 1, wherein the stoichiometric ratio of isocyanate moieties of the phenyl-containing isocyanate compound to the boron compound is about 1:1 to about 1:100.

12. The method according to claim 1, wherein the stoichiometric ratio of isocyanate moieties of the phenyl-containing isocyanate compound to the boron compound is about 1:1.

13. The method according to claim 1, wherein the aprotic solvent is selected from the group consisting of methylene chloride, chloroform, benzene, toluene, xylene, ethyl ether, methyl ether, tetrahydrofuran, p-dioxane and acetonitrile.

14. The method according to claim 1, wherein the reaction occurs with heating up to about 100° C. or the boiling point of the solvent if the boiling point is lower than 100° C.

15. The method according to claim 1, wherein neutralization occurs in the presence of an aqueous base.

16. The method according to claim 15, wherein the aqueous base is selected from the group consisting of sodium carbonate, sodium bicarbonate and sodium hydroxide.

17. The method according to claim 1, wherein the reaction proceeds until $CO_2$ evolution substantially ceases.

18. The method according to claim 1, wherein phenyl isocyanate is reacted with $H_2O$ and boron trifluoride etherate, the ratio of phenyl isocyanate to $H_2O$ being about 1:1 and the ratio of phenyl isocyanate to boron trifluoride etherate being about 1:1 in ethyl ether with heating to a temperature of about 30° C. at atmospheric pressure until $CO_2$ evolution substantially ceases, and neutralizing the aryl amide in the presence of an aqueous saturated sodium carbonate solution.

* * * * *